(12) United States Patent
Liang et al.

(10) Patent No.: US 10,227,293 B2
(45) Date of Patent: Mar. 12, 2019

(54) METHOD FOR PREPARING CITALOPRAM DIOL INTERMEDIATE

(71) Applicants: Zhejiang Huahai Pharmaceutical Co., Ltd, Linhai (CN); Zhejiang Huahai Licheng Pharmaceutical Co., Ltd, Linhai (CN); Zhejiang Huahai Jiancheng Pharmaceutical Co., Ltd, Linhai (CN)

(72) Inventors: Zunjun Liang, Linhai (CN); Weifeng Xiao, Linhai (CN); Caihua Peng, Linhai (CN); Wenfeng Huang, Linhai (CN); Guoliang Tu, Linhai (CN)

(73) Assignees: Zhejiang Huahai Pharmaceutical Co., Ltd, Linhai (CN); Zhejiang Huahai Licheng Pharmaceutical Co., Ltd, Linhai (CN); Zhejiang Huahai Jiancheng Pharmaceutical Co., Ltd, Linhai (CN)

( * ) Notice: Subject to any disclaimer, the term of this patent is extended or adjusted under 35 U.S.C. 154(b) by 0 days.

(21) Appl. No.: 15/580,517

(22) PCT Filed: Jun. 9, 2015

(86) PCT No.: PCT/CN2015/081054
§ 371 (c)(1),
(2) Date: Dec. 7, 2017

(87) PCT Pub. No.: WO2016/197320
PCT Pub. Date: Dec. 15, 2016

(65) Prior Publication Data
US 2018/0162805 A1    Jun. 14, 2018

(51) Int. Cl.
*C07C 253/30* (2006.01)
*C07C 255/59* (2006.01)
*C07B 49/00* (2006.01)
*C07F 3/02* (2006.01)

(52) U.S. Cl.
CPC ............ *C07C 253/30* (2013.01); *C07B 49/00* (2013.01); *C07C 255/59* (2013.01); *C07F 3/02* (2013.01); *C07B 2200/07* (2013.01)

(58) Field of Classification Search
CPC .................................................. C07C 253/30
See application file for complete search history.

(56) References Cited

U.S. PATENT DOCUMENTS 4,650,884 A    3/1987    Bogeso

FOREIGN PATENT DOCUMENTS

| CN | 101538257 | 9/2009 |
|---|---|---|
| CN | 102675152 | 9/2012 |
| CN | 104072390 | 10/2014 |
| EP | 0347066 | 12/1989 |
| WO | WO 2006/106531 | 10/2006 |

OTHER PUBLICATIONS

International Search Report and Written Opinion Issued in International Application No. PCT/CN2015/081054, dated Mar. 16, 2016.
Extended European Search Report issued in Corresponding European Patent Application No. 15894590.7, dated Jan. 4, 2019.
Zong et al., "Added-Metal-Free Catalytic Nucleophilic Addition of Grignard Reagents to Ketones" *The Journal of Organic Chemistry*, 2012, 77:4645-4652.

*Primary Examiner* — Shawquia Jackson
(74) *Attorney, Agent, or Firm* — Norton Rose Fulbright US LLP

(57) ABSTRACT

The present invention relates to a method for preparing a citalopram diol represented by formula IV, comprising the following steps: in the existence of an auxiliary reagent of metal salt, allowing 5-cyanophthalide to sequentially subjected to Grignard addition reactions with p-fluorophenyl magnesium halide and N, N-dimethylaminopropyl magnesium halide in an organic solvent; and after the reactions are completed, performing hydrolysis and separation to obtain citalopram diol represented by formula IV. In the present invention, by adding an auxiliary reagent of metal salt, the activity and the selectivity of the Grignard reactions are remarkably improved, and the reaction yield is obviously enhanced.

9 Claims, No Drawings

METHOD FOR PREPARING CITALOPRAM DIOL INTERMEDIATE

CROSS REFERENCE TO RELATED APPLICATIONS

This application is a national phase under 35 U.S.C. § 371 of International Application No. PCT/CN2015/081054, filed Jun. 9, 2015. The contents of the referenced application are incorporated into the present application by reference.

FIELD OF INVENTION

The present invention relates to a method for preparing a key intermediate for citalopram and S-citalopram diol.

BACKGROUND OF INVENTION

Citalopram is a kind of important antidepressant, and is a selective serotonin (5-HT) reuptake inhibitor. It has advantages such as rapid onset, obvious antidepressant effect, and little side effects, etc. Its isomer having single optical activity, escitalopram (S-citalopram), has anti-proliferative effect 100 times of that of its isomer with an opposite configuration, R-citalopram. Therefore, escitalopram (S-citalopram) has better efficacy and smaller dosage. Currently, S-citalopram gradually occupies larger market share of antidepressants. The structures of citalopram (I) and its isomer having single optical activity, i.e. S-citalopram (II), are as follows:

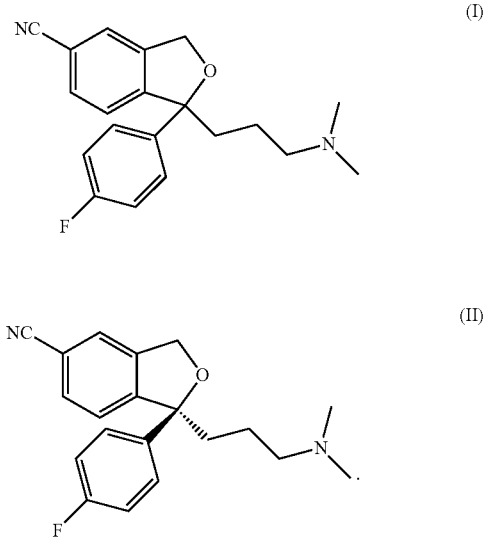 [SMILES: CN(C)CCCC1(c2ccc(F)cc2)OCc2cc(C#N)ccc21 ; CN(C)CCC[C@@]1(c2ccc(F)cc2)OCc2cc(C#N)ccc21]

A main route for preparing citalopram is cyclizing citalopram diol (IV) to obtain citalopram (I).

A main route for preparing S-citalopram is obtaining S-citalopram diol (V) through chiral resolution of citalopram diol (IV), and then cycling S-citalopram diol (V) to obtain S-citalopram (II).

The structural formulae of citalopram diol (IV) and S-citalopram diol (V) are as follows:

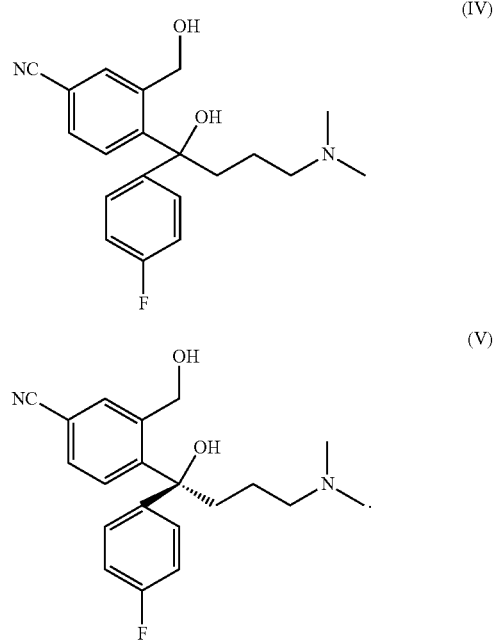 [SMILES: CN(C)CCCC(O)(c1ccc(F)cc1)c1ccc(C#N)cc1CO ; CN(C)CCC[C@](O)(c1ccc(F)cc1)c1ccc(C#N)cc1CO]

It follows that citalopram diol (IV) is a key intermediate for the industrial production of citalopram and S-citalopram.

U.S. Pat. No. 4,650,884 reports that citalopram diol (IV) is obtained by using 5-cyanophthalide as the starting material, which is subjected to two Grignard addition reactions with p-fluorophenyl magnesium halide and N,N-dimethyl-aminopropyl magnesium halide. The synthetic route is as follows:

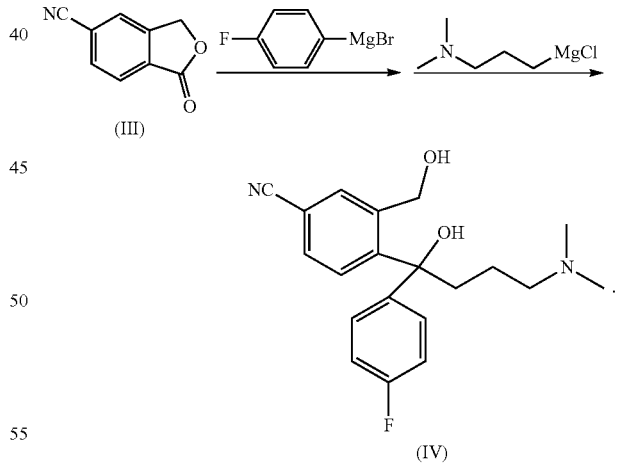

The method reported in the above patent mainly suffers from low conversion rate, substantial side reactions, low yield, and low purity of the product. The possible reasons are as follows: (1) there are many reaction sites for the Grignard addition reactions, and the selectivity of the reactions is poor; (2) the intermediate obtained after the first addition with p-fluorophenyl magnesium halide is a ketone, resulting in a large steric hindrance during the following addition with N,N-dimethylaminopropyl magnesium halide, and thus the conversion rate is low; and (3) competitive reactions exist between the two Grignard reagents, which result in many by-products.

SUMMARY

The present invention provides an efficient method for preparing a key intermediate of citalopram diol (IV), comprising the following steps:

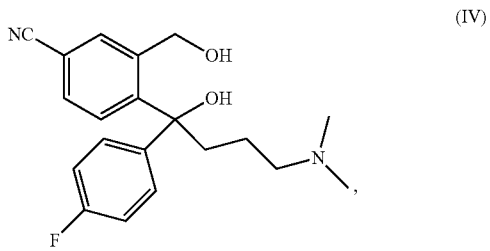

performing Grignard addition reactions of 5-cyanophthalide successively with p-fluorophenyl magnesium halide and N,N-dimethylaminopropyl magnesium halide in an organic solvent; after end of the reaction, hydrolyzing and separating to obtain free base of citalopram diol represented by formula IV; optionally, further converting the compound of formula IV into its acid salt;

the Grignard reactions described above are carried out in the presence of an auxiliary reagent of metal salt $M_A X_B$, wherein M is selected from the group consisting of Mn, Cu, Zn, Li, or Cs, X is selected from the group consisting of Cl, Br, or I, A is 1, and B is 1 or 2, and the auxiliary reagent of metal salt $M_A X_B$ is preferably $MnCl_2$, CuI, $ZnCl_2$, LiCl, or LiBr.

In one embodiment, the molar ratio of the auxiliary reagent of metal salt $M_A X_B$ to 5-cyanophthalide is preferably ≥0.2, more preferably from 0.2 to 2.0, still more preferably from 0.3 to 1.8, even more preferably from 0.4 to 1.5, and further preferably from 0.5 to 1.0.

In another embodiment, the p-fluorophenyl magnesium halide is p-fluorophenyl magnesium bromide.

In yet another embodiment, the N,N-dimethylaminopropyl magnesium halide is N,N-dimethylaminopropyl magnesium chloride. In another embodiment, the organic solvent is preferably tetrahydrofuran, 2-methyltetrahydrofuran, cyclopentyl methyl ether, methyl tert-butyl ether, isopropyl ether, and diethyl ether, and further preferably tetrahydrofuran.

The present invention also provides a method for preparing citalopram or S-citalopram, comprising further converting the citalopram diol represented by formula IV obtained according to the method of the present invention into citalopram or S-citalopram. The methods for converting citalopram diol into citalopram or S-citalopram are described in the prior art, for example, EP 0347066 B1 and CN 101538257 A.

Without being bound by any theory, the present inventors surprisingly found that during the Grignard addition reactions of 5-cyanophthalide successively with p-fluorophenyl magnesium halide and N,N-dimethylaminopropyl magnesium halide in an organic solvent, the activity and selectivity of the Grignard reactions can be significantly improved by the addition of an auxiliary reagent of metal salt ($M_A X_B$), for example:

(1) the site selectivity of the reaction is significantly improved, so that few side reactions are rendered, for example, the content of the main reaction product of the present invention is greater than 80%;

(2) the activity of the addition reaction of dimethylaminopropyl-Grignard reagent can be remarkably increased, thereby the conversion rate of the Grignard reaction increases, for example, the conversion rate of the Grignard reaction of the present invention is greater than 90%; and (3) the yield is significantly increased.

DETAILED DESCRIPTION

The present invention will now be described in more detail by way of example so that the object, technical solutions, and advantages of the invention are more clear. Obviously, the described examples are only part of the examples of the present invention, rather than all of the examples. Based on the examples of the present invention, all the other examples obtained by those skilled in the art without creative efforts are within the protection scope of the present invention.

EXAMPLES 1-15

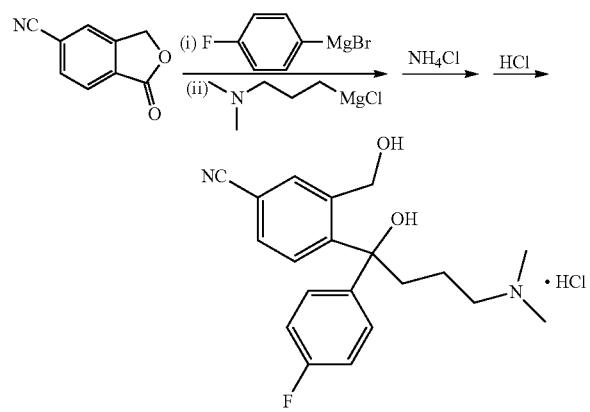

5-cyanophthalide (31.8 g, 1.0 equiv.), tetrahydrofuran (300 ml), and a certain amount of metal salt $M_A X_B$ were added. The reactants were cooled to −5° C., and the reaction was carried out under stirring for 0.5 hour. At a temperature controlled at −5 to 0° C., 300 ml of a solution of p-fluorophenyl magnesium bromide in tetrahydrofuran (0.8 mmol/ml, 1.2 equiv.) was slowly added dropwise. After the addition, the reaction was carried out under stirring for 1 hour while maintaining the temperature. The temperature was raised to 5° C. and controlled between 5 to 10° C. 260 ml solution of N,N-dimethylaminopropyl magnesium chloride in tetrahydrofuran (1.0 mmol/ml, 1.3 equivalent) was slowly added dropwise. After the addition, the reaction was carried out under stirring for 0.5 hour while maintaining the temperature. The reaction solution was added into 500 mL of saturated aqueous solution of ammonium chloride, and stirred for 2 hours. The organic layer was separated. The aqueous layer was extracted twice with toluene 200 ml×2. The organic layers were combined, washed twice with water 200 ml×2, and concentrated to dry. A sample was taken and tested with HPLC for the conversion rate of the reaction and the purity of the main product in the reaction solution. 400 ml of toluene was added to the dry product. The mixture was heated to 50° C., and stirred till clear. 100 ml of water was added to the mixture. The aqueous layer was adjusted with concentrated hydrochloric acid to a pH of 4.0-5.0, and separated. The toluene layer was further extracted once with 50 ml of water. The aqueous layers were combined, and cooled to 5° C. A large amount of solid was precipitated. The mixture was stirred for 60 minutes while maintaining the temperature, and filtered. The filter cake was dried under vacuum at 50° C. to give citalopram diol hydrochloride. The yield was calculated. Different equivalents and types of metal salt $M_A X_B$, and different organic solvents are used for performing the above experiment. The results are shown in the following table:

| Example No. | Metal salt $M_A X_B$ | Equivalent weight of metal salt, $M_A X_B$, relative to 5-cyano-phthalide | Organic solvent | Conversion rate of reaction | Purity of main product in reaction liquid | Yield |
|---|---|---|---|---|---|---|
| 1 | MnCl$_2$ | 1.0 | tetrahydrofuran | 97% | 86% | 84% |
| 2 | MnBr$_2$ | 0.5 | 2-methyl-tetrahydrofuran | 98% | 81% | 75% |
| 3 | MnI$_2$ | 0.5 | cyclopentyl methyl ether | 97% | 83% | 72% |
| 4 | LiCl | 2.0 | methyl tert-butyl ether | 98% | 87% | 83% |
| 5 | LiCl | 0.5 | isopropyl ether | 98% | 87% | 82% |
| 6 | LiCl | 0.2 | tetrahydrofuran | 95% | 82% | 76% |
| 7 | LiBr | 1.0 | tetrahydrofuran | 98% | 82% | 77% |
| 8 | LiI | 1.0 | 2-methyl-tetrahydrofuran | 97% | 81% | 72% |
| 9 | CsI | 0.5 | cyclopentyl methyl ether | 92% | 84% | 70% |
| 10 | ZnCl$_2$ | 1.0 | methyl tert-butyl ether | 98% | 85% | 80% |
| 11 | CuCl$_2$ | 1.0 | isopropyl ether | 96% | 81% | 70% |
| 12 | CuBr | 0.5 | tetrahydrofuran | 95% | 85% | 73% |
| 13 | CuI | 0.5 | tetrahydrofuran | 97% | 87% | 76% |
| 14 | MnCl$_2$ | 0.7 | 2-methyl-tetrahydrofuran | 96% | 87% | 83% |
| 15 | CuBr$_2$ | 0.8 | cyclopentyl methyl ether | 97% | 86% | 82% |

Comparative Example 1 (without Metal Salt)

5-cyanophthalide (31.8 g, 1.0 equiv.) and tetrahydrofuran (300 ml) were added. The reactants were cooled to −5° C., and the reaction was carried out under stirring for 0.5 hour. At a temperature controlled at −5 to 0° C., 300 ml of a solution of p-fluorophenyl magnesium bromide in tetrahydrofuran (0.8 mmol/ml, 1.2 equiv.) was slowly added dropwise. After the addition, the reaction was carried out under stirring for 1 hour while maintaining the temperature. The temperature was raised to 5° C., and controlled between 5 to 10° C. 260 ml of a solution of N,N-dimethylaminopropyl magnesium chloride in tetrahydrofuran (1.0 mmol/ml, 1.3 equiv.) was slowly added dropwise. After the addition, the reaction was carried out under stirring for 0.5 hour while maintaining the temperature. The Grignard reaction solution was added to 500 mL of saturated aqueous solution of ammonium chloride, and stirred for 2 hours. The organic layer was separated. The aqueous layer was extracted twice with toluene 200 ml×2. The organic layers were combined, washed twice with water 200 ml×2, and concentrated to dry. A sample was taken and tested with HPLC. The conversion rate of the reaction was 77% and the purity of the main product in the reaction solution was 69%. 400 ml of toluene was added to the dry product. The mixture was heated to 50° C., and stirred till clear. 100 ml of water was added to the mixture. The aqueous layer was adjusted with concentrated hydrochloric acid to a pH of 4.0-5.0, and separated. The toluene layer was further extracted once with 50 ml of water. The aqueous layers were combined, and cooled to 5° C. A large amount of solid was precipitated. The mixture was stirred for 60 minutes while maintaining the temperature, and filtered. The filter cake was dried under vacuum at 50° C. to give citalopram diol hydrochloride. The yield was 61%.

Comparative Example II (U.S. Pat. No. 4,650,884)

5-cyanophthalide (31.8 g, 1.0 equiv.) and tetrahydrofuran (300 ml) were added. The reactants were cooled to −3° C., and the reaction was carried out under stirring for 0.5 hour. At a temperature controlled at −3 to 0° C., 300 ml of a solution of p-fluorophenyl magnesium bromide in tetrahydrofuran (0.8 mmol/ml, 1.3 equiv.) was slowly added dropwise. After the addition, the reaction was carried out under stirring for 0.5 hour while maintaining the temperature. The cold bath was removed. The mixture was stirred overnight. The temperature was controlled between 10 to 12° C. 200 ml of a solution of N,N-dimethylaminopropyl magnesium chloride in tetrahydrofuran (1.0 mmol/ml, 1.0 equiv.) was slowly added dropwise. After the addition, the cold bath was removed. The mixture was stirred overnight at room temperature. The Grignard reaction solution was added to ice water, and adjusted with acetic acid to a pH of 6.5-7.0. Tetrahydrofuran was distilled off. 300 mL of toluene was added. The reaction solution was adjusted with saturated aqueous solution of ammonium chloride to a pH of 9.0. The toluene layer was separated. The aqueous layer was further extracted once with 200 ml of toluene. The toluene layers were combined, and washed once with 200 ml of hot water at 50° C. A sample of toluene layer was taken and tested with HPLC. The conversion rate of the reaction was 75%, and the purity of the main product in the reaction solution was 65%. The toluene layer was further extracted once with aqueous solution of acetic acid. 300 ml of toluene was added. The mixture was adjusted with aqueous ammonia to pH>9.0. The aqueous layer was extracted once with 200 ml of toluene. The toluene layers were combined, and concentrated to dry. The concentrate was absorbed with active carbon and silica gel, and purified. The purified product was salified with HBr to give 38.1 g of citalopram diol hydrochloride. The yield was 45%.

By comparing the above examples with the comparative examples, it can be seen that during the Grignard addition reactions of 5-cyanophthalide successively with p-fluorophenyl magnesium halide and N, N-dimethylaminopropyl magnesium halide in an organic solvent, the activity and selectivity of the specific Grignard addition reactions can be significantly improved by the addition of an auxiliary reagent of metal salt ($M_AX_B$). For example, in the case that the auxiliary reagent of metal salt ($M_AX_B$) according to the present invention is not added, the conversion rate of the reaction is only 77%, and the yield is only 61%, according to Comparative Example 1; the conversion rate of the reaction is only 75%, and the yield is only 45%, according to Comparative Example 2. However, in the case that the auxiliary reagent of metal salt ($M_AX_B$) according to the present invention is added, the conversion rate of the reaction was remarkably increased to 92% or above, even up to 98%, and the yield was remarkably increased to 70% or above, even up to 84%. Such results are completely unexpectable by those skilled in the art.

The foregoing are only preferred examples of the invention, and are not intended to limit the present invention. Any modifications, equivalent substitutions, improvements and the like made within the spirit and principle of the present invention are within the protection scope of the present invention.

What is claimed is:

1. A method for preparing citalopram diol represented by formula IV, comprising the following steps:

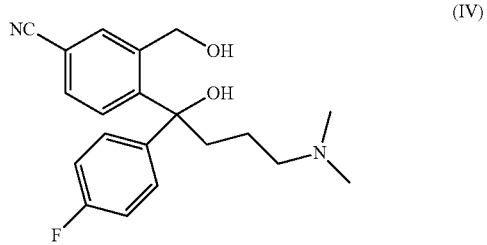 [SMILES: CN(C)CCCC(O)(c1ccc(F)cc1)c1ccc(C#N)cc1CO]

(IV)

performing Grignard addition reactions of 5-cyanophthalide successively with p-fluorophenyl magnesium halide and N,N-dimethylaminopropyl magnesium halide in an organic solvent; after the reaction, hydrolyzing and separating to obtain free base of citalopram diol represented by formula IV; optionally, further converting the compound of formula IV into its acid salt;

characterized in that the Grignard reaction is carried out in the presence of an auxiliary reagent of metal salt $M_AX_B$, wherein M is selected from the group consisting of Mn, Cu, Zn, Li, or Cs, X is selected from the group consisting of Cl, Br, or I, A is 1, and B is 1 or 2.

2. The method according to claim 1, wherein the auxiliary reagent of metal salt $M_AX_B$ is $MnCl_2$, CuI, $ZnCl_2$, LiCl, and LiBr.

3. The method according to claim 1, wherein the molar ratio of the auxiliary reagent of metal salt $M_AX_B$ to 5-cyanophthalide is ≥0.2.

4. The method according to claim 3, wherein the molar ratio of the auxiliary reagent of metal salt $M_AX_B$ to 5-cyanophthalide is from 0.5 to 1.0.

5. The method according to claim 1, wherein the p-fluorophenyl magnesium halide is p-fluorophenyl magnesium bromide.

6. The method according to claim 1, wherein N,N-dimethylaminopropyl magnesium halide is N,N-dimethylaminopropyl magnesium chloride.

7. The method according to claim 1, wherein the organic solvent is selected from the group consisting of tetrahydrofuran, 2-methyltetrahydrofuran, cyclopentyl methyl ether, methyl tert-butyl ether, isopropyl ether, or diethyl ether.

8. The method according to claim 7, wherein the organic solvent is tetrahydrofuran.

9. A method for preparing citalopram or S-citalopram, characterized in further converting the citalopram diol represented by formula IV obtained according to the method of claim 1 into citalopram or S-citalopram, wherein the citalopram is obtained by cyclizing the citalopram diol, and the S-citalopram is obtained by cyclizing S-citalopram diol prepared by chiral resolution of the citalopram diol.

* * * * *